(12) United States Patent
Grone et al.

(10) Patent No.: US 6,902,728 B1
(45) Date of Patent: Jun. 7, 2005

(54) CHEMOKINE RECEPTOR ANTAGONIST AND CYCLOSPORIN IN COMBINED THERAPY

(75) Inventors: Hermann-Joseph Grone, Munich (DE); Peter J. Nelson, Munich (DE); Amanda Proudfoot, Chens sur Leman (FR); Timothy N. C. Wells, Prevessin Moens (FR)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/787,335

(22) PCT Filed: Sep. 16, 1999

(86) PCT No.: PCT/EP99/06844

§ 371 (c)(1),
(2), (4) Date: Jun. 13, 2001

(87) PCT Pub. No.: WO00/16796

PCT Pub. Date: Mar. 30, 2000

(30) Foreign Application Priority Data

Sep. 18, 1998  (EP) .............................................. 98117697

(51) Int. Cl.$^7$ .......................... A61K 38/19; A61K 38/13
(52) U.S. Cl. .......................... 424/85.1; 514/11; 514/12; 514/885; 530/324
(58) Field of Search ............................ 424/85.1, 145.1, 424/143.1; 514/11, 12, 885; 530/324, 350

(56) References Cited

FOREIGN PATENT DOCUMENTS

| WO | 9617935 | 6/1996 |
| WO | 9705896 | 2/1997 |
| WO | 9806703 | 2/1998 |
| WO | 9806751 | 2/1998 |

OTHER PUBLICATIONS

Pattison et al. Rantes chemokine expression in cell–mediated transplant rejection of the kindney. The Lancet. 1994. Vol.343, pp. 209–211.*
Elias et al. Structure, Function and Inhibition of Chemokines. Annual Pharmacology and Toxicology. Vol.42, pp. 469–499. 2002.*
J.M. Pattison, et al., "Rantes Chemokine Expression in Transplant–Associated Accelerated Atherosclerosis", *Journal of Heart And Lung Transplantation*, (Dec. 1996), 15 (12), pp. 1194–9.
H.J. Grone, et al., "Met–Rantes Reduces Vascular And Tubular Damage During Acute Renal Transplant Rejection: Blocking Monocyte Arrest And Recruitment", *FASEB Journal*, (Aug. 1999) 13 (11), pp. 1371–1383.
P.J. Nelson, "Chemokines and Chemokine Receptors in Renal Transplant Rejection", *European Cytokine Network*, (1999) 10/2 (305–306).

"Immunopathology of renal allograft rejection analyzed with monoclonal antibodies to mononuclear cell markers"; G. A. Bishop, et al.; *Kidney International*; vol. 29 (1986); pp. 708–717.
"Leukocyte–Endothelial Cell Recognition: Three (or More) Steps to Specificity and Diversity"; Eugene C. Butcher; *Cell*; vol. 67; Dec. 20, 1991; pp. 1033–1036.
"Lymphocyte Homing and Homeostasis"; E. Butcher, et al.; *Science*; vol. 272; Apr. 5, 1996; pp. 60–66.
"Acute vascular rejection: a clinical and morphological study"; M.C.R. Castro, et al.; *Transpl. Int.*; 1998; 11 [Suppl. 1]: S15–S18.
"Production of the RANTES Chemokine in Delayed–type Hypersensitivity Reactions: Involvement of Macrophages and Endothelial Cells"; O. Devergne, et al.; *J. Exp. Med.*; vol. 179; May 1994; pp. 1689–1694.
"Adhesion properties of Mono Mac 6, a monocytic cell line with characteristics of mature human monocytes"; W. Erl, et al.; *Artherosclerosis*; 113 (1995); pp. 99–107.
"Microvascular surgical techniques in research, with special reference to renal transplantation in the rat"; B. Fisher, et al.; *Surgery*; vol. 58, No. 5; Nov. 1965; pp. 904–913.
"RANTES and MCP–3 Antagonists Bind Multiple Chemokine Receptors"; J. Gong, et al.; *The Journal of Biological Chemistry*; vol. 271, No. 18; May 3, 1996; pp. 10521–10527.
"Histopathology of the renal allograft"; H.–J. Grone; *Neph. Dial. Transplant*; 11; 1996; pp. 1916–1917.
"Molecular Mechanisms of Monocyte Adhesion to Interleukin–1β–Stimulated Endothelial Cells Under Physiologic Flow Conditions"; S. Kukreti, et al.; *Blood*; vol. 89, No. 11; Jun. 1, 1997; pp. 4104–4111.
"Rantes and Monocyte Chemoattractant Protein–1 (MCP–1) Play an Important Role in the Inflammatory Phase of Crescentic Nephritis, but Only MCP–1 is Involved in Crescent Formation and Interstitial Fibrosis"; C. Lloyd, et al.; *J. Exp. Med.*; vol. 185, No. 7; Apr. 7, 1997; pp. 1371–1380.
"Role of MCP–1 and RANTES in inflammation and progression of fibrosis during murine crescentic nephritis"; C. Lloyd, et al.; *Journal of Leukocyte Biology*; vol. 62, Nov. 1997; pp. 676–680.
"Activation and regulation of chemokines in allergic airway inflammation"; N.W. Lukacs, et al.; *Journal of Leukocyte Biology*; vol. 59; Jan. 1996; pp. 13–17.

(Continued)

*Primary Examiner*—Prema Mertz
*Assistant Examiner*—Fozia Hamud
(74) *Attorney, Agent, or Firm*—Browdy and Neimark

(57) ABSTRACT

The use of a chemokine receptor antagonist together with a cyclosporin to produce a pharmaceutical composition for treating or preventing rejection of transplanted organs, tissues or cells is herein disclosed. Said pharmaceutical compositions for the simultaneous, sepatate or sequential use of its active ingredients for the above specified therapy are also disclosed and claimed. In particular, the use of Met-RANTES together with cyclosporin A to produce a pharmaceutical composition for the treatment of renal allograft transplant rejection is experimentally shown.

16 Claims, 2 Drawing Sheets

OTHER PUBLICATIONS

"L–and P–Selectins, but Not CD49d (VLA–4) Integrins, Mediate Monocyte Initial Attachment to TNF–α–Activated Vascular Endothelium Under Flow in Vitro"; F. Luscinskas, et al.; *The Journal of Immunology*; 156; 1996; pp. 326–335.

"Chemokines—Chemotactic Cytokines That Mediate Inflammation"; Andrew D. Luster; vol. 338, No. 7; Feb. 12, 1998; pp. 436–445.

"Cyclosporin"; *Martindale, The Extra Pharmacopoeia*; 31st edition; London, Royal Pharmaceutical Industry; 1996; pp. 557–562.

"Chemokines, lymphocytes and viruses: what goes around, comes around"; P. Nelson, et al.; *Curr. Opin., Immunol.*; 10, 1998; pp. 265–270.

"Rantes"; P. Nelson, et al.; *Cytokines, Handbook of Immunopharmacology Series*; London; 1998; pp. 433–448.

"Cloning and Characterization of a Novel Promiscuous Human β–Chemokine Receptor D6"; R. Nibbs, et al.; *The Journal of Biological Chemistry*; vol. 272, No. 51; Dec. 19, 1997; pp. 32078–32083.

"Manipulation of Cytokine Networks in Transplantation"; P. Nickerson, et al.; *Transplantation*; vol. 63, No. 4; Feb. 27, 1997; pp. 489–494.

"The chemokine receptor CXCR3 mediates rapid and shear–resistant adhesion–induction of effector T lymphocytes by chemokines IP10 and Mig"; L. Piali, et al.; *Eur. J. Immunol.*; 28; 1998; pp. 961–972.

"Effect of CC chemokine receptor anatagonist on collagen induced arthritis in DBA/1 mice"; C. Plater–Zyberk, et al.; *Immunology Letters*; vol. 57; 1997; pp. 117–120.

"Extension of Recombinant Human RANTES by the Retention of the Initiating Methionine Produces a Potent Antagonist"; A. Proudfoot, et al.; *The Journal of Biological Chemistry*; vol. 271, vol. 5; Feb. 2, 1996; pp. 2599–2603.

"Chemokines and renal disease"; D. Schlondorff, et al.; *Kidney International*; vol. 51; 1997; pp. 610–621.

"The cytokine response in renal allograft rejection"; R.L. Schmouder, et al.; *Nephrol. Dial. Transplant*; 10 [Suppl 1]; 1995; pp. 36–43.

"Potent Inhibition of HIV–1 Infectivity in Macrophages and Lymphocytes by a Novel CCR5 Antagonist"; G. Simmons, et al.; *Science*; vol. 276; Apr. 11, 1997; pp. 276–279.

"Expression of vascular endothelial growth factor and its receptors in human renal ontogenesis and in adult kidney"; M. Simon, et al.; *Am. J. Physio.*; 268; 1995; pp. F240–F250.

"Traffic Signals for Lymphocyte Recirculation and Leukocyte Emigration: The Multistep Paradigm"; T. Springer, et al.; *Cell*; vol. 76; Jan. 28, 1994; pp. 301–314.

"Enhanced Renal Allograft Rejection by Inhibitors of Nitric Oxide Synthase: A Nonimmunologic Influence of Alloreactivity"; T. Stojanovic, et al.; *Laboratory Investigation*; vol. 74, No. 2; Feb. 1996; pp. 496–512.

"The Th1/Th2 paradigm and the allograft response"; T. Strom, et al.; *Curr. Opin. Immunol.*; 8; 1996; pp. 688–693.

"Chemokine–induced Eosinophil Recruitment: Evidence of a Role for Endogenous Eotaxin in an In Vivo Allergy Model in Mouse Skin"; M. Teixeira, et al.; *J. Clin. Invest.*; vol. 100, No. 7; Oct. 1997; pp. 1657–1666.

"Immunobiology of Renal Transplantation"; J. Valente, et al.; *Surgical Clinics of North America*; vol. 78, No. 1 Feb. 1998; pp. 1–26.

"RANTES Chemokine Empression in Diseased and Normal Human Tissues"; I. von Leuttichau, et al.; *Cytokine*; vol. 8, No. 1; Jan. 1996; pp. 89–98.

"Neutrophil Accumulation on Activated, Surface–adherent Platelets in Flow is Mediated by Interaction of Mac–1 with Fibrinogen Bound to α11bβ3 and Stimulated by Platelet–activated Factor"; C. Weber, et al.; *J. Clin. Invest.*; vol. 100, No. 8; Oct. 1997; pp. 2085–2093.

"Tumor necrosis factor induces enhanced responeses to platelet–activating factor and differentiation in human monocytic Mono Mac 6 cells"; C. Weber, et al.; *Eur. J. Immunol.*; 23; 1993; pp. 852–859.

"Inhibitors of Protein Tyrosine Kinase Suppress TNFStimulated Induction of Endothelial Cell Adhesion Molecules"; C. Weber, et al.; *The Journal of Immunology*; 155; 1995; pp. 445–451.

"Monocyte haptotaxis induced by the RANTES chemokine"; C. Wiedermann, et al.; *Current Biology*; vol. 3, No. 11; 1993; pp. 735–739.

"Establishment of a Human Cell Line (Mono Mac 6) with Characteristics of Mature Monocytes"; H. W. Lomms Ziegler–Heitbrock, et al.; *Int. J. Cancer*; vol. 41; 1988; pp. 456–461.

* cited by examiner (a)

(b)

CHEMOKINE RECEPTOR ANTAGONIST AND CYCLOSPORIN IN COMBINED THERAPY

FIELD OF THE INVENTION

The present invention relates to the use of a chemokine receptor antagonist together with a cyclosporin to produce a pharmaceutical composition for treating or preventing rejection of transplanted organs, tissues or cells. It also relates to said pharmaceutical compositions for the simultaneous, separate or sequential use of its active ingredients for the above specified therapy.

In particular, it relates to the use of Met-RANTES together with cyclosporin A to produce a pharmaceutical composition for the treatment of renal allograft transplant rejection.

BACKGROUND OF THE INVENTION

The mechanisms by which a T cell response to a foreign (allogeneic or xenogeneic) protein or cell or organ is mounted are fairly well understood. Antigen presenting cells (APCs) are attracted to areas of inflammation or damage (that may be induced by surgical transplantation). The repertoire of T cells in the periphery is constantly surveying tissues for evidence of pathogens or the presence of foreign (allo- or xenogeneic) tissue. Once any of these warning signals are recognised, the APCs engulf the protein, digest it and present it to the host's immune system.

The immune system is well equipped to rapidly identify foreign, diseased or inflamed tissue and rapidly destroys it. This has always been a major barrier to tissue, organ and cell transplantation as well as gene therapy. Major problems are generally associated with chronic inmmunosuppression, encapsulation or immunoisolation. The unwanted side effects of chronic immunosuppression include increased susceptibility to opportunistic infection and tumour formation.

In particular, acute renal allograf rejection is mediated by both alloantigen-dependent and -independent factors and is characterised by a mononuclear cell infiltrate consisting mainly of T lymphocytes, monocyte/macrophages and occasional eosinophils (Grone H. J., 1996, Valente J. F. et al., 1998, Bishop G. A. et al., 1986). The recruitment of these leukocytes from the peripheral circulation into the transplanted organ involves a complex interplay between a series of molecules expressed on the leukocyte and endothelial surface (Butcher E. C., 1991, Butcher E. C. et al., 1996, Springer T. A., 1994).

The desire for long-term acceptance of grafted tissue in the absence of continuous immunosuppression is a long-standing goal in human medicine.

Chemokines, a large superfamily of structurally related cytokines, have been shown to selectively promote the rapid adhesion, chemotaxis and activation of specific leukocyte effector subpopulations (Springer T. A., 1994, Nelson P. J. et al., 1998, Luster A. D., 1998. Schlöndorff D. et al., 1997).

Chemokines are characterised by a series of shared structural elements including the conserved cysteine residues used to define the C, C—C, C—X—C and C—$X_3$—C chemokine subgroups (where X represents an intervening amino acid residue between the first two amino terminal proximal cysteines). All of the various biological actions of chemokines appear to be directed through their interaction with a large family of seven-transmembrane spanning, C-protein coupled receptors (Nelson P. J. et al., 1998, Luster A. D., 1998, Schlöndorff D. et al., 1997). The cell type specific expression of these receptors appears to control a significant degree, the leukocyte specificity of chemokine action (Nelson P. J. et al, 1998, Luster A. D., 1998, Schlöndorff D. et al., 1997).

The chemokine RANTES (regulated upon activation, normal T-cell expressed and secreted), a member of the C—C chemokine subfamily, is a ligand for a number of chemokine receptors including CCR1, CCR3, CCR5, CCR9 and DARC (Duffy Antigen Receptor for Chemokines) in humans (Nelson P. J. et al., 1998, Luster A. D., 1998, Schlöndorff D. et al., 1997, Nibbs R. J. et al., 1997). RANTES is a potent chemoattractant for T cells, monocytes, natural killer cells, basophils and eosinophils (Nelson P. J. et al., 1998).

Chemokines such as RANTES, are thought to play pivotal roles in the cellular infiltrates that underlie various disease processes. For example, RANTES is expressed in vivo in diseases characterised by a mononuclear cell infiltrate including, delayed-type hypersensitivity, necrotizing glomerulonephritis, inflammatory lung disease and renal allograft rejection (Schlöndorff D. et al., 1997, Nelson P. J. et al., 1998, Devergne O. et al., 1994, Luckas N. W. et al., 1996, Lloyd C. M. et al., 1997, Pattison J. et al., 1994, Wiedermann C. J. et al., 1993). In studies of human kidneys undergoing acute cellular rejection, RANTES protein was found localised to mononuclear infiltrating cells, renal tubular epithelial cells and tile endothelium of peritubular capillaries (Pattison J. et al., 1994, Wiedermann C. J. et al., 1993). Since acute cellular rejection is characterised by an intravascular mad interstitial cellular infiltrate consisting of monocyte/macrophages, T lymphocytes and occasional eosinophils, RANTES is potentially a key player in the pathogenesis of acute rejection (Schlöndorff D. et al., 1997, Nelson P. J. et al., 1998, Pattison J. et al., 1994, Wiedermann C. J. et al., 1993).

Based upon these observations a model for the role of RANTES in renal allograft rejection was proposed (Nelson P. J. et al., 1998, Pattison J. et al., 1994, Wiedermann C. J. et al., 1993). Early in rejection, the microvascular endothelium becomes inflamed, platelets degranulate, releasing RANTES protein that binds to the endothelial surface. The inflamed renal tubules and endothelial cells produce additional chemokines including RANTES. The accumulated surface bound chemokines then provide directional signals to circulating leukocytes as they roll across the endothelial surface (Butcher E. C., 1991, Butcher E. C. et al., 1996, Springer T. A., 1994, Nelson P. J. et al., 1998, Pattison J. et al., 1994, Wiedermann C. J. et al., 1993). Leukocytes recognise the surface bound protein, upregulate integrins, and firmly adhere to the endothelial surface, undergo diapedesis and extravasation. As the leukocytes become activated, they produce additional cytokines and chemokines thus amplifying and propagating the inflammatory response (Nelson P. J. et al., 1998, Pattison J. et al., 1994, Wiedermann C. J. et al., 1993).

Modification of the amino terminus of the RANTES protein can dramatically alter its properties (Proudfoof A. E. et al., 1996, Gong J. H. et al., 1996, Simmons G. et al., 1997). The addition of a single methionine residue changes the agonist protein into a RANTES receptor antagonist with nanomolar potency (Proudfoof A. E. et al., 1996). This antagonist, Met-RANTES, is bioactive in mouse and rat (Proudfoot unpublished), and has been shown to suppress inflammation in murine models of allergic skin and rheumatoid arthritis and to partially inhibit in necrotizing glomerulonephritis (Teixeira M. M et al., 1997, Plater-Zyberk C. et al., 1997, Lloyd C. M et al., 1997).

Cyclosporins represent a group of nonpolar cyclic oligopeptides, having imnnunosuppressant activity, produced by the fungus *Tolypocladium inflatum* Gams and other fungi imperfecti. The major component, cyclosporin A, has been identified along with several other minor metabolites, cyclosporins B through N. A number of synthetic analogues have also been prepared. Cyclosporin A is a commercially available drug, which has attained widespread clinical application as immunosuppressant in organ transplantation procedures.

The main problem with cyclosporin A has been its nephrotoxicity (Martindale, 1996), characterised by fluid retention, increased serum creatinine and urea concentrations, a fall in glomerular filtration rate, and decreased sodium and potassium excretion. In particular, in renal graft recipients may be difficult to distinguish nephrotoxicity from graft rejection.

DISCLOSURE OF THE INVENTION

We have now found that a combined treatment with a chemokine receptor antagonist and a low dose of a cyclosporin results in a reduction of the inflammatory events associated with transplant rejection, as compared to treatment with a cyclosporin alone.

In particular, we have found that Met-RANTES reduced damage to vascules and tubules and caused a significant reduction of interstitial rejection in renal allograft transplantation.

Therefore, the main object of the present invention is the use of a chemokine receptor antagonist in combination with a cyclosporin to produce a pharmaceutical composition for treating or preventing the rejection of transplanted organs, tissues or cells. The chemokine receptor antagonist and the cyclosporin can be administered simultaneously, separately or sequentially.

Another object of the present invention is, therefore, the method for treating or preventing the rejection of transplanted organs, tissues or cells by administering simultaneously, separately or sequentially an effective amount of a chemokine receptor antagonist and an effective amount of a cyclosporin, together with a pharmaceutically acceptable excipient.

An "effective amount" refers to an amount of the active ingredients that is sufficient to affect the course and the severity of the rejection of transplanted organs, tissues or cells, leading to the reduction or remission of such pathology. The effective amount will depend on the route of administration and the condition of the patient.

A further object of the present invention are the pharmaceutical compositions containing a chemokine receptor antagonist and a cyclosporin, in the presence of one or more pharmaceutically acceptable excipients, for the simultaneous, separate or sequential administration of its active ingredients for treating or preventing the rejection of transplanted organs, tissues or cells.

In case of separate or sequential use of the two active ingredients, the pharmaceutical compositions of the invention will consist of two different formulations, each comprising one of the two active ingredients together with one or more pharmaceutically acceptable excipients.

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Besides the pharmaceutically acceptable carrier, the compositions of the invention can also comprise minor amounts of additives, such as stabilisers, excipients, buffers and preservatives.

The administration of such active ingredients may be by intravenous, intramuscular or subcutaneous route. Other routes of administration, which may establish the desired blood levels of the respective ingredients, are comprised by the present invention.

The combined therapy of the present invention is suitable for treating or preventing the rejection of any transplanted organ, tissue or cell, but it is particularly advisable in cases of kidney transplantations, due to the nephrotoxicity of cyclosporin A.

The term "chemokine receptor antagonist" means any molecule, which acts as antagonist to the mature full-length naturally-occurring chemokines and, preferably, does not show significant chemoattractant activity. For the measurement of said chemoattractant activity reference is made for example to (Nelson P. J. et al., 1998).

The chemokine receptor antagonist is preferably selected among truncated RANTES molecules reported in International patent application WO 97/44462, truncated MCP-3, RANTES (missing the first five, six, seven, eight or nine amino acid residues) and MIP-1α described in International patent application WO 98/06751, truncated RANTES (missing the first two amino acid residues) and MCP-2 described in European patent application No. 9711663.8 or N-terminally extended RANTES (Met-RANTES, Leu-RANTES, and Gln-RANTES) described in WO 96/17935. Met-RANTES is particularly preferred. To the above-cited patent applications, reference is made also for the methods of preparation of the chemokine receptor antagonists mentioned.

The cyclosporin is selected among cyclosporin A, metabolites or synthetic analogues thereof. Preferably, it is cyclosporin A.

Therefore, a preferred embodiment of the invention consists in the combined use of Met-RANTES and cyclosporin A for treating or preventing the rejection of kidney allograft transplantation. In this case, the Applicant has found that it is possible to reduce the effective dose of cydosporin and this is a great advantage considering the dose-dependent toxicity to the kidney which is known to be associated with the cyclosporin treatment.

The above effect has been showed with in vivo experiments on rats.

The invention will now be described by means of the following Examples, which should not be construed as in any way limiting the present invention. The Examples will refer to the Figures specified here below.

EXAMPLES

Materials and Methods

Cells Used

Figure 1:
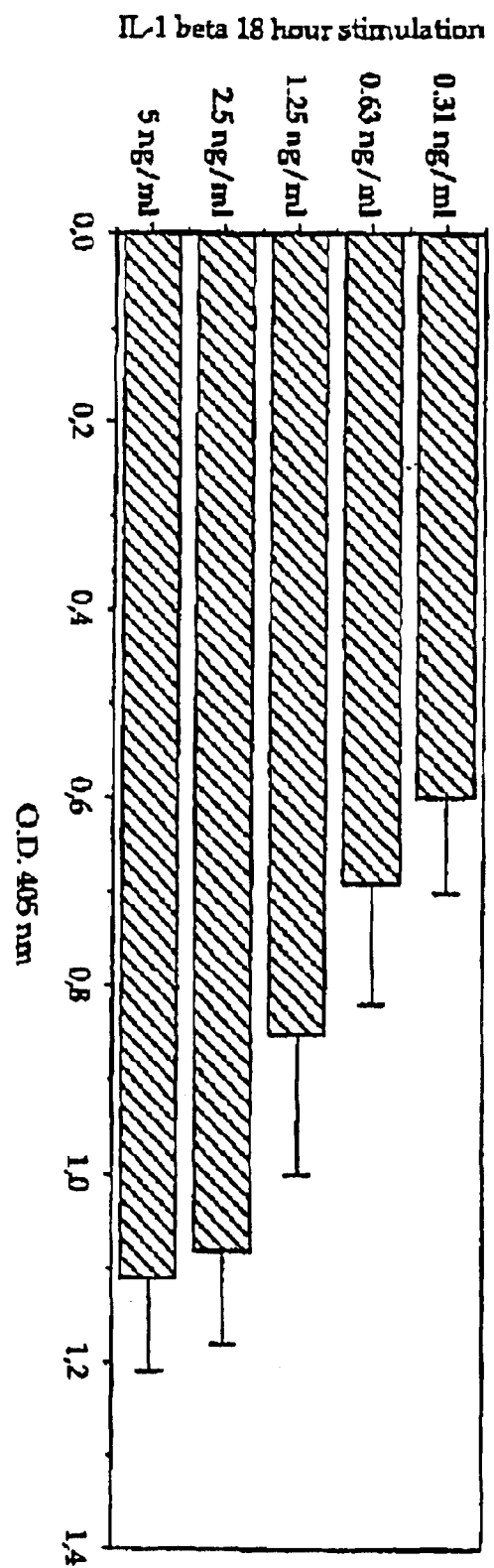
FIG. 1. The ability of RANTES to bind directly to microvascular endothelium before and after 12 hours stimulation with IL-1β (5 ng/ml) was determined. DMVEC was grown on 96 well plates and RANTS measured using a modified ELISA procedure.

The monocytic tumour cell line MonoMac 6 was cultured in RPMI 1640 with 10% FCS supplemented as previously described (Ziegler-Heitbrock H. W .L. et al., 1988). The cells were routinely carried in 24-well plates (Costar) and the media and sera tested for low LPS content. Primary human dermal microvascular endothelial cell (DMVEC) from human neonatal forskin were obtained from Dr. K. Degitz (Dermatology, LMU, Munich, Germany). The cells were carried in MCDB 131 media (Gibco BRL, Eggenstein Germany) supplemented with 10% Fetal calf serum (Boehringer Mannheim, Germany), 1 mg/ml Hydrocortisone acetate (Sigma, Deisenhofen, Germany), 5×10$^5$ M Dibutyryladenosinemonophosphate (Sigma, Deisenhofen, Germany), 2 mM Glutamine (Seromed, Berlin, Germany), 100 U/ml Penicillin, 100 mg/ml Streptomycin, 25 mg/ml Amphtericin B (antibiotic/Antimycotic Sol. Gibco BRL, Eggenstein, Germany) and incubated at 37° C. and 5% CO2. The cells were grown on T75 flasks, 35 mm Petri plates (Costar, Corning, N.Y.) or 96 well flat bottom plates (Nunc, Wiesbaden, Germany) precoated with 0.5% gelatine (Sigma, Deisenhofen, Germany). Medium was changed every 2–3 days. Cells were characterised, and purity of cultures was ensured through morphologic appearance and immunofluorescence flow cytometry for CD31 surface expression.

Materials

Materials for histologic studies were obtained from Merck (Darmstadt, Germany). Materials for chemical and immunologic measurements were supplied by Sigma (Munich, Germany). IL-1β and TNFα were purchased from Sigma (Munich, Germany). Generation of recombinant RANTES and the RANTES specific monoclonal antibody VL1 were described previously (Von Luettichau 1., 1996). Met-RANTES was produced and endotoxin removed for in vivo studies as described previously (Proudfoof A. E. et al., 1996, Teixeira M. M et al., 1997, Plater-Zyberk C. et al., 1997, Lloyd C. M et al., 1997).

Animals and Renal Transplantation

Inbred male rats were used in all experiments. Lewis (LEW, RT1$^1$) rats served as recipients of Fisher 344 (F344 RT1$^{1v1}$) or Brown Norway (BN RT1*) kidneys. The animals were purchased from Charles River GmbH, Sulzfeld, Germany. The rats weighed 190 to 250 gm (Lew and F344) and 140 to 170 gm (BN) to adjust for ureter diameter. Transplantation was performed using a modification of the technique originally described by Fisher and Lee (Fisher B. et al., 1965). Briefly, the animals were anaesthetised by ether-drop anaesthesia, the donor kidney was flushed with 5 ml of cold 0.91% NaCl (4° C.) with or without 100 μg Met-RANTES. The kidney and ureter were removed en bloc including the renal artery with a 5-mm aortic cuff and the renal vein with a 3-mm vena cava patch. The kidneys were stored in 0.91% NaCl 4° C.

The donor kidney was transplanted to the abdominal aorta and inferior vena cava of the recipient animal, below the left renal artery, by end-to-side anastomoses with 8-0 nonabsorbable monofilament nylon suture. Ureter anastomosis was performed end-to-end with 11-0 nonabsorbabie monofilament nylon suture. Total ischemic time of the donor kidney varied between 30 and 40 min. Hyronephrosis was evaluated both macroscopically at time of death and by light microscopy. All animals with hyronephrosis were excluded from the experimental groups. The left kidney of the recipient was always removed at the time of transplantation. In the Fisher to Lewis transplantation the right kidney was left in plate to have an internal control for the effects of Met-RANTES. In Brown Norway to Lewis transplantations a bilateral nephrectomy was performed at the time of transplantation.

Experimental Groups:

Experimental groups were as follows:

Group 1: Fisher 344 kidney into Lewis rat with one endogenous kidney.

Group 1a: with Met-RANTES 200 μg/day for 7 days (n=9)

Group 1b: without Met-RANTES for 7 days (n=9)

Group 2: Brown Norway kidney into bilaterally nephrectomised Lewis rat with CyA 2.5 mg/kg BW administrated per day.

Group 2a: with Met-RANTES, 50 μg/day for 12 days (n=4)

Group 2b: without Met-RANTES for 12 days (n=4)

Cyclosporin A (CyA) (kindly provided by Sandoz, Basel, Switzerland) was dissolved in olive oil and administered subcutaneously in a concentration of 2.5 mg/kg BW per day for 12 days, starting 4 h post-transplantation. Met-RANTES was dissolved in water and adjusted to 0.9% sodium chloride and injected once daily intravenously at a dose of 200 μg per day in Fisher to Lewis and at a dose of 50 μg per day in Brown Norway to Lewis transplantation experiments.

Serum Analysis

Blood taken from the aorta at the time of sacrifice was analysed for creatinine, urea, glucose, and bilirubin using an automated serum analyser. This did not provide information on renal function for the Fisher to Lewis model as the transplanted animals had one endogenous kidney, but these measurements were relevant in the Brown Norway to Lewis transplant model.

Histology

Organs (lung, liver, kidney, and spleen) were removed under deep anaesthesia. The organs were quickly blotted free of blood, weighed, and then processed as needed for histology, immnunohistochemistry, or in situ hybridisation. The organs were cut into 1-mm slices and either immersion-fixed in 4% formaldehyde in phosphate buffered saline (PBS) pH 7.35, (PBS: 99 mM $NaH_2PO_4×H_2O$, 108 mM $NaH_2PO_4×2H_2O$ and 248 mM NaCl) for 24 h or fixed in methacam for 8 h and embedded in paraffin, or frozen in liquid nitrogen and consequently stored at −80° C. until used for immunohistochemistry. Light microscopy was performed on 3 μm sections stained by periodic acid-Schiff or Goldner-Elastica.

Immunohistochemistry

The monoclonal antibody ED1 (Serotech/Camon, Wiesbaden, Germany) was used on methacam fixed paraffin embedded tissue (3 μm) to demonstrate monocytes/ macrophages. For detection for CD8 antigen expressed on cytotoxic T lymphocytes, monoclonal mouse antibodies were applied to frozen sections after ice cold acetone-fixation for 5 min (Serotech/Camon, Wiesbaden, Germany). An alkaline phosphatase anti-alkaline phosphatase detection system was applied (Dako, Hamburg, Germany). Controls, omitting the first or second antibody for each section tested, were negative.

Morphometry

Vascular injury score: Preglomerular vessels with endothelial damage, thrombus and endothelialitis were assessed as showing no injury (0), a mild (1), moderate (2) and severe (3) degree of injury and evaluated in whole kidney section including cortex, outer and inner medulla. A degree specific vascular injury index was defined as the percentage of vessels with the respective degree of injury encountered in a whole kidney section. Total vascular injury score was calculated as the sum of all vessels, with all degrees of vascular injury, whereby the number of vessels with degree one, was multiplied by one, that of degree two, by a factor of two, and that of degree three, by a factor of three (Stojanovic T. et al., 1996). Tubular inflammation score: Tubular damage was evaluated as non-existent (0), mild (1), moderate (2) and severe (3) as judged in 20 High power Fields (HPF) of cortex and cuter stripe of outer medulla. The total tubular damage score was calculated as described for the total vascular injury score, Interstitial inflammation score: The extent of interstitial infiltration by mononuclear cells was judged as non-existent (0), mild (1), moderate (2) and severe (3) and the total score calculated as described for the total vascular injury score. The number of monocycles/ macrophages and T cells within capillary convolutes of glomeruli was calculated as the mean of the respective numbers in all glomeruli in one kidney section In Situ Hybridisation Single-stranded RNA probes were generated by in vitro transcription of a cDNA clone of rat RANTES (Dr. H Sprenger, Marburg, Germany). In vitro transcription was carried out using a Trans-Probe-T kit (Pharmacia, Freiburg, Germany) and digoxigenin-labeled uridine triphosphate (Boehringer, Mannheim, Germany). The vector (pBluescript KS (+) Stratagene, Heidelberg, Germany) was cut with BamHI and transcribed with T3-RNA polymerase to yield antisense probe, to yield sense probe, the plasmid was cut with EcoRI followed by transcription with T7 RNA polymerase. After deparaffinization, kidney sections were digested with 20 μg/ml proteinase K (Boehringer) m PBS for 16 min. Sections were postfixed for 5 min in 4% formaldehyde and acetylated (0.25% acetic anhydride in 0.1 M triethanolamine, 10 min). For in situ hybridisation with digoxigenin labelled mRNA, the following hybridization buffer was used: 5×standard saline citrate (SSC), 50% formanide, 50 μg/ml tRNA, 50 μg/ml heparin, and 0.1% sodium dodecylsulfate.

After hybridisation at 56° C. for 16 h, slides were washed once in 4×SSC and 2×SSC for 10 min at 37° C., followed by a washing step in 0.55×SSC for 30 min and 0.1 SSC at 22° C. for 15 min Antidigoxigenin antibody incubation and alkaline phosphatase reaction was carried out according to guidelines by the manufacturer (Boehringer, Mannheim, Germany), taking nitro-blue tetrazolium and 5-bromo-4-chloro-3-indolylphosphate as colour reagents (Stojanovic T. et al., 1996, Simon M. et al., 1995).

RNase Protection Assay

Total RNA was isolated from whole rat kidney as previously described (Simon M. et al., 1995). RNase protection experiments were performed using a commercial RPA kit (PharMingen, San Diego, Calif., probe rCK-1). This kit allowed the simultaneous measurement of mRNA species for rat: IL-1α, IL-1β, TNF-α, TNF-β, IL-2, IL-3, IL4, IL-5, IL-6, IL-10 and IFN-γ and the housekeeping genes, GAPDH and L32. 20 μg of total RNA was used for each determination. The protected samples were run out on a precast gel (Quickpoint™ Rapid Nucleic Acid Separation System used according to the manufactures recommendations, Novex, San Diego, Calif.). The intensity of the specific bands were quantitated using a Molecular Dynamics Storm 840 Phosphorimager, normalized to L32 gene expression, and averaged over the three animals analysed.

In Vitro Binding Assay

The DMVEC were grown to confluency on coated 96 well flat bottom plates, The resultant endothelial monolayer was either left untreated or treated with various concentrations of IL-L1β (0.1 to 5 ng/ml) for 12 h. The RANTES binding assay was a modification of a previously described procedure (Pattison J. et al., 1994, Wiedermann C. J. et al., 1993). Horseradish, peroxidase (HRP) conjugated anti-human-RANTES monoclonal antibody VL1 (0.1 μg) was pre-incubated at 25° C. for 30 min with an excess of recombinant human RANTES (20 μg/ml) in DMVEC growth media (without supplements). The chemokine-antibody complex was added then used to assay the relative chemokine binding capacity of the microvascular endothelium. The endothelial monolayer was gently washed 1× with unsupplemented growth media (25° C.) and the chemokine-antibody complex was added and incubated at 25° C. for 30 min. The wells were then washed four times with media without sera at 25° C. The HRP reaction was developed for 5 min or less. The optical density at 406 nm of the plate was determined using an ELISA plate reader. The results demonstrate changes in the binding capacity of the inflamed microvascular endothelium for RANTES protein following activation of the endothelial cells. All experiments were performed in quadruplicate and the results displayed are representative of three separate experiments.

Florescence Activated Cell Sorting (FACS) Analysis

Flow cytometry analysis of dermal microvascular cells (DMVEC) was performed essentially as described (Weber C. et al., 1995). Briefly, confluent DMVEC stimulated with IL-Iβ (5 ng/ml), or left untreated for 12 h, were trypsinized, reacted with IL-saturating concentrations of ICAM-1 mAb RR1/1 (kindly provided by Dr. R. Rothlein), E-selectin mAb, VCAM-1 mAb (both Serotec), or isotype control for 30 min on ice, stained with fluorescein isothiocyanate (FITC)-conjuzated goat anti-mouse IgG (Boehringer Mannheim), and analysed in a FACScan (Becton Dickinson). After correction for unspecific binding, data were expressed as specific mean log fluorescence intensity (sMFI) in channels.

In Vitro Model System of Monocyle Recruitment on Microvascular Endothelium Under Physiological Flow Conditions.

The interaction of monocytes with DMVEC was studied in laminar flow assays performed essentially as descried (Weber C. et al., 1997, Kukerti S. et al., 1997, Piali L. et al., 1998). Briefly, DMVEC were grown to confluence in 35 mm Petri dishes, and stimulated with IL-1β (5 ng/ml) or left untreated for 12 h. The plates were assembled as the lower wall m a parallel wall flow chamber and mounted on the stage of an Olympus IMT-2 inverted microscope with 20× and 40× phase contrast objectives. Monotypes (MonoMac 6 cells) were cultured as reported (Ziegler-Heitbrock H. W. L. et al., 1988, Weber C. et al., 1993) and resuspended at $10^6$/ml in assay buffer (HBSS) containing 10 mM Hepes/pH 7.4 and 0.5% HAS. Shortly before assay, 1 mM $Mg^{2+}$ and 1 mM $Ca^{2+}$ was added. The cell suspensions were kept in a heating block at 37° C. during the assay and were perfused into the flow chamber at a rate of 1.5 dyn/cm for 5 min. For inhibition experiments, monocytes were preincubated with Met-RANTES at different concentrations (0.01–1 μg/ml) for 30 min on ice. The number of firmly adherent cells after 5 rain was quantified in multiple fields (at least 5 per experiment) by analysis of images recorded with a long integration JVC 3CCD video camera and a JVC SR L 900 E video recorder, and were expressed as cells/$mm^2$. The type of adhesion analysed was restricted to primary, i.e. direct interactions of monocytes with endotbelium. As an inverse measure of firm arrest, the number of cells rolling at reduced velocity on endothelium was determined within the last 30 sec. of the 5 min intervals, and were assessed as the percentage of all interactions in the field. The number of cells spreading or transmigrating after 5 min intervals was determined in high power fields as described (Luscinskas F. W. et al., 1994), and expressed as percentage of cells firmly attached.

Statistical Analysis

Values are given ms roman +/− SEM. Statistical analysis was performed using the Mann-Whithney U-Wilcoxon rank sum test. A p value <0.05 was considered as showing a significant difference between two groups.

Results

Allotransplantation of Fisher 344 (F344 $RT1^{1v1}$) kidneys into Lewis (LEW. $RT1^1$)

The transplantation of Fisher (344) rat kidneys into Lewis rats in the absence of immunosuppression resulted in a characteristic mononuclear cell infiltrate and tissue damage by day 7 following surgery. Histological examination showed local mononuclear cell infiltration of the intima of preglomerular arteries, and tubular interstitium. The major component of this interstitial mononuclear infiltrate consisted of monocyte/macrophage cells. The degree of damage to arteries, arterioles, tubules, and the extent of mononuclear cell infiltration of the interstitium was graded on a scale from non existent (0), mild (1), moderate (2), to severe (3), using a previously described procedure based upon semiquantitative morphometry (see Materials and Methods).

The effect of Met-RANTES on this process was examined by treating transplanted animals with daily intravenous injections of Met-RANTES at 200 μg per animal. The initial injection of Met-RANTES was given within 1 hour following formation of the vascular anastomosis during transplantation surgery. No additional immune suppressive agent was given during the course of the experiment. Light microscopy and immunohistology showed no obvious effect of Met-RANTES treatment on the endogenous kidney.

During organ transplant rejection, the transplanted organ generally increases in weight due to inflammation. The results summarised in Table 1, show that the Met-RANTES treated animals had a statistically significant reduction in transplanted organ weight relative to the untreated animals. The results also suggested a reduction in T cell and monocyte infiltration of glomeruli, however, this reduction was not considered statistically significant (Mann-Whitney U-Wilcoxon rank sum test). The most profound effects of Met-RANTES treatment are summarised in Table 2. The data demonstrate a significant reduction in the vascular injury and tubular rejection score of the Met-RANTES treated animals relative to that seen in the untreated animals. While the general trend regarding interstitial rejection score showed an apparent reduction in the Met-RANTES treated animals, this could not be considered statistically significant (Mann-Whithney U-Wilcoxon rank sum test).

Histological sections and immunohistochemical stains were examined to evaluate the effects of Met-RANTES on the rejection process. The kidneys were removed seven days following transplantation and prepared as described in Materials and Methods.

Vascular damage with mononuclear cells present within the lumen and the wall of arteries were observed in untreated kidneys. In contrast, Met-RANTES treated animals showed no vascular rejection. The interstitial region of untreated animals demonstrated infiltration of a large number of dark staining mononuclear cells within the interstitium and tubules. By contrast, Met-RATES treated animals demonstrated reduced mononuclear infiltration, less tubular damage with a well-developed red brush border of proximal tubules.

Localisation of Rat RANTES mRNA by In Situ Hybridisation

Tissue sections taken from rejecting Fisher rat kidneys were used in in situ hybridisation studies to demonstrate cell specific expression of RANTES mRNA in the rejecting kidney. The results were similar to those previously described for RANTES expression during rejection of human renal allografts (Pattison J. et al., 1994, Wiedermann C. J. et al., 1993, Von Luettichau I., 1996). Strong expression by infiltrating mononuclear cells and renal tubules and limited but identifiable expression by some endothelial cells was seen.

Met-RANTES Treated Animal Show a Reduction in the Expression of Proinflammatory Cytokine mRNA as Determined by RNase Protection Assays The increased expression of Proinflammatory cytokines such as IL-1α, IL-1β, IL-2-, IL-3, IL-6, TNFβ, TNFα and IFNγ is characteristic of renal transplant rejection (Nickerson P. et al., 1997. Schmouder R. L. et al., 1995, Strom T. B. et al., 1996, Castro M. D. et al., 1998). The expression of these cytokines is an indication of an ongoing inflammatory process. We examined the effect of Met-RANTES on the expression of a series of cytokine in transplanted Fisher rat kidneys using quantitative RNase protection assays. Whole organ RNA samples were isolated from normal control kidneys, untreated transplanted kidneys and Met-RANTES treated transplanted kidneys. The mRNA levels representing the cytokines: IL-1α, IL-1β, TNFβ, TNFα, IL-2, IL-3, IL-4, IL-5, IL-6, IL-10 and IFNγ, were determined relative to the internal standards L32 and GAPDH. The results show that seven days following transplantation, the untreated kidneys upregulated mRNAs coding for IL-1α (24 fold), TNFβ (3.2 fold) and IFNγ (1.7) with the most pronounced increase seen in IL-1β (8.4 fold) and TNFα (4.6 fold). No mRNA expression of IL-2, IL-4, or IL-5 was detected in these kidneys at this time point (7 days post transplantation). The corresponding Met-RANTES treated animals showed a reduced average expression of IL-1α (25%), IL-1β (48%), TNFβ (34%), TNFα (24%) and IFNγ (24%) relative to the untreated animals.

Transplantation of Brown Norway Rat Kidneys into Lewis Rats: Effect of Met-RANTES in Conjunction with Low Dose Cyclosporin A (CyA).

We then expanded the experiments to determine if Met-RANTES could complement low dose CyA treatment in renal transplant rejection. For this procedure, we chose a renal transplant model that would yield a more vigorous rejection episode, namely, the transplantation of Brown Norway kidney into the Lewis rat. A bilateral nephrectomy was performed at the time of transplantation. The level of CyA used, 2.5 mg/kg of body weight administered subcutaneously per day, was previously shown not to significantly block renal rejection in this model (Gröne unpublished results (Stojanovic T. et al., 1996)). Finally, to better detect any synergistic action, a reduced dose of Met-RANTES, 50 µg per animal per day, was used in these experiments. The results summarised in Table 3 show a statistically significant reduction in the vascular and tubular damage seen in the Met-RANTES/low dose-CyA treated animals as compared to the animals that were only treated with the low dose-CyA. In addition, a significant reduction in mononuclear cell infiltration of the interstitial region was seen. These histological observations were confirmed by functional measurements where serum creatinine was reduced in the Met-RANTES treated animals relative to the untreated controls (0.98±0.12 vs. 1.42+0.17 mg %, (n=3)).

Direct RANTES Binding and Adhesion Molecule Expression on Activated Microvascular Endothelium Since a reduction of monocyte infiltration into vascular luminal spaces represented a prominent feature of Met-RANTES treatment in both transplantation models, we set out to study potential mechanisms for this effect. In the model of the role of RANTES in renal transplant rejection, it was speculated that RANTES protein, released by activated platelets or secreted by locally inflamed tissue, accumulates on the surface of inflamed endothelium where it may support monocyte recruitment (Nelson P. J. et al., 1998, Pattison J. et al., 1994, Wiedermann C. J. et al., 1993). To study the direct binding of RANTES to microvascular endothelium, we examined the capacity of activated dermal microvascular endothelium (DMVEC) to sequester RANTES protein using a modification of an assay previously employed to detect endothelial surface binding of RANTES in tissue sections (Pattison J. et al., 1994, Wiedermann C. J. et al., 1993). An HRP-conjugated mAb specific for RANTES, VL1, was incubated with an excess of RANTES protein, and the resulting complex was added to resting or IL-1β-activated microvascular endothelium grown in 96 well flat bottom culture plates. Using an ELISA-like format, the capacity of DMVEC to bind the antigen-mAb complex as opposed to mAb alone was determined. While the microvascular endothelium could bind some RANTES protein without prestimulation, the binding was greatly increased following prestimulation with the proinflammatory cytokine IL-1α (FIG. 1). The background staining of uncomplexed mAb to unstimulated or activated endothelium was negligible.

To further characterise the inflammatory activation of microvascular endothelium, the surface expression of molecules involved in monocyte adhesion, i.e. E-selectin and the Ig superfamily members ICAM-1 and VCAM-1, were determined on DMVEC using a previously established flow cytometry procedure (Weber C. et al., 1995). The analysis revealed that resting DMVEC expressed constitutive surface levels of ICAM-1, however little VCAM-1 or E-selectin was detected (Table 4). Activation of DMVEC with IL-1 for 12 h resulted in an upregulation of ICAM-1 expression and a marked induction of VCAM-1 and E-selectin surface expression (Table 4).

Met-RANTES Blocks the Firm Adhesion of Monocytes to Inflamed Microvascular Endothelium but do not Effect Subsequent Events in Diapedesis.

In an attempt to gain insight into potential mechanisms of action of Met-RANTES, we studied whether a blockade of RANTES receptors could inhibit the firm arrest and diapedesis of monocytes on microvascular endothelium. To this end, we used monocytic MonoMac 6 cells that show the adhesive characteristics and integrin repertoire of mature monocytes, and express several chemokine receptors including CCR1 (Erl W. et al., 1995). DMVEC were grown to confluence on Petri dishes which were either left unstimulated or were activated with IL-1β (5 ng/ml) for 12 h. The microvascular endothelium was then tested in a parallel wall flow chamber where the MonoMac 6 cells were perfused through the chamber at a shear rate of 1.5 dyn/cm$^2$ for 5 min. Under such physiological flow conditions, MonoMac 6 cells undergo short periods of rolling, and the attachment of a proportion of cells can be readily converted into shear-resistant arrest. After 5 min of accumulation, the number of MonoMac 6 cells that had undergone firm adhesion to the endothelium was determined (FIG. 2(a)).

Figure 2:
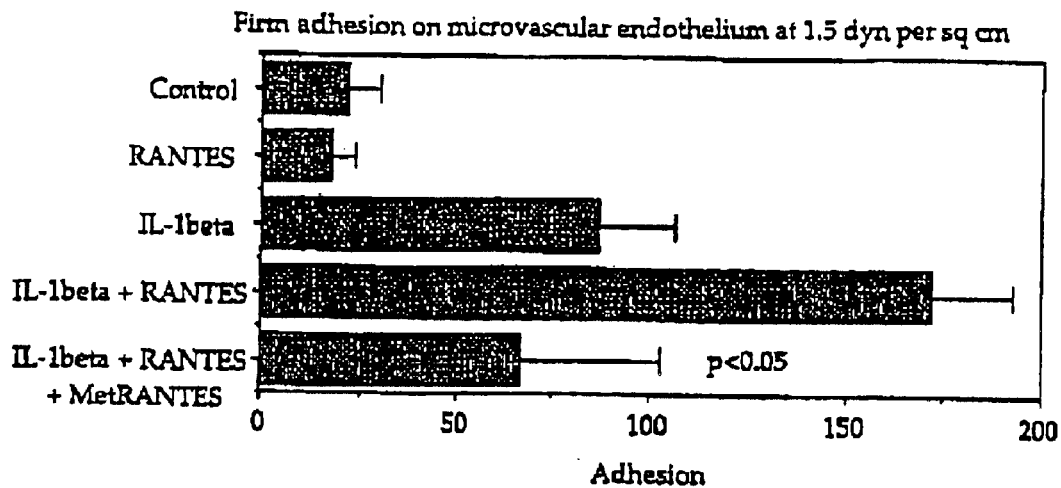
FIGS. 2a and b: The effects of Met-RANTES on firm arrest, spreading or transmigration of MonoMac 6 cells on activated microvascular endothelium under physiological flow. DMVEC grown to confluence in Petri dishes were stimulated with IL-1β (5 ng/ml) or left untreated (control) for 12 hours, and pre-incubated with or without RANTES (10 ng/ml) for 30 minutes. MonoMac 6 cells were pre-treated with or without Met-RANTES (1 μg/ml) for 30 minutes, and perfused at a constant flow rate of 1.5 dyn/cm$^2$. (a) Firm adhesion to DMVEC was determined by counting the number of firmly adherent monocytes in multiple fields after a 5 minutes period, and expressed as cells/mm$^2$. (b) Monocytes undergoing spreading or transmigration were counted after 5 minutes in multiple high power fields, and expressed as the percentage of initially firmly adherent cells. Data represent mean±SD of 3 independent experiments. (Note: the results were reproducible over a range of Met-RANTES from 0.01 to 1 μg/ml).
Figure 2:
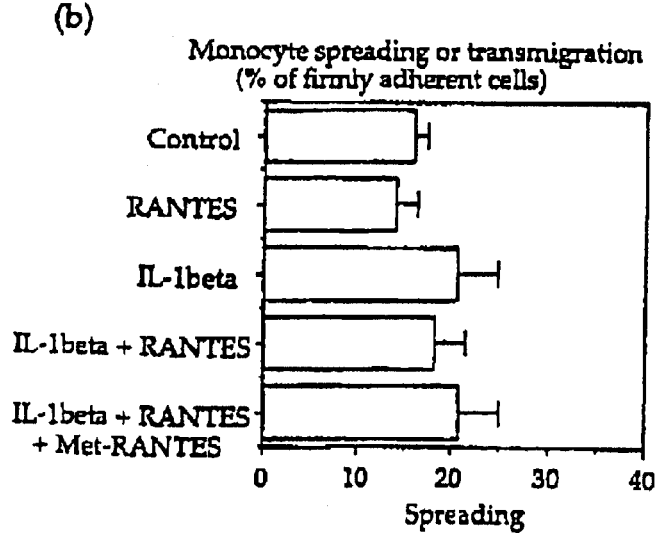

Few monocytic cells firmly adhered to unstimulated microvascular endothelium and the pre-exposure of the endothelial cells to RANTES protein showed no significant effect. Prestimulation of the microvascular endothelium with IL-1β resulted in an increase in shear resistant adhesion of monocytes. Inhibition with mAb confirmed previous findings that this process is mediated by monocyte α4 and β2 integrins that interact with ICAM-1 and VCAM-1 expressed on activated endothelium, respectively (Kukerti S. et al., 1997, Luscinskas F. W. et al., 1994). Consistent with the immobilisation of RANTES in direct binding assays, pre-exposure of IL-1β-activated microvascular endothelium to RANTES protein markedly enhanced the firm arrest and accumulation of monocytes within 5 min (FIG. 2a). Notably, pre-incubation of monocytes with Met-RANTES at various concentrations (0.01–1 µg/ml) completely blocked RANTES-mediated shear resistant adhesion of monocytes on IL-1β activated DMVEC (FIG. 2a, and data not shown), in parallel, the fraction of monocytes rolling on the activated microvascular endothelium which can be used as an inverse measure of firm arrest, was reduced after preexposure to RANTES, but was restored by Met-RANTES, indicating that the number of initial interactions with the activated endothelium was unaffected. After firm arrest, a fraction of monocytes underwent shape change or spreading, and some ultimately migrated in-between or under endothelial cells. However, RANTES or Met-RANTES did not alter spreading or transmigration (FIG. 2b), inferring the involvement of other signals. Thus, these results indicate that Met-RANTES may reduce monocyte recruitment during renal transplant rejection by blocking monocyte arrest to inflamed microvascular endothelium.

TABLES

TABLE 1

Fisher and rat kidney transplanted into Lewis rats. The number of monocytes/macrophages and T cells within capillary convolutes of glomeruli was calculated as the mean of the respective numbers in all glomeruli in one kidney section.

|  | Control (n = 9) | Met-RANTES (n = 9) |
| --- | --- | --- |
| Body Weight (g) | 211.8 ± 5.15 | 195 ± 5.98 |
| Transplant-Kidney Weight | 1.41 ± 0.048 | 1.15 ± 0.08* |
| Endogenous Kidney Weight | 0.91 ± 0.04 | 0.8 ± 0.04 |
| T Cells in Glomeruli | 3.98 ± 0.81 | 2.75 ± 0.45 |
| Macrophages in Glomeruli | 9.16 ± 1.69 | 5.98 ± 0.87 |

*Indicates significant (p < 0.05) difference between the groups tested.

TABLE 2

Fisher kidney transplanted into Lewis rats. Summary of histological and immunohistological analysis of the effects of Met-RANTES on vascular damage, and interstitial mononuclear infiltration.

|  | Vascular Injury | | Tubular Damage | | Interstitial Inflammation | |
| --- | --- | --- | --- | --- | --- | --- |
|  | Control | Met-RANTES | Control | Met-RANTES | Control | Met-RANTES |
| Grade0 | 50.67 ± 9.02 | 85.5 ± 2.66 | 15.56 ± 6.03 | 46.00 ± 12.15 | 1.39 ± 1.11 | 16.00 ± 7.14 |
| Grade 1 | 40.44 ± 5.5 | 12.8 ± 4.17 | 32.22 ± 8.25 | 30.00 ± 6.06 | 44.17 ± 12.39 | 58.00 ± 8.7 |
| Grade 2 | 4.44 ± 2.22 | 0.9 ± 0.6 | 20.56 ± 5.68 | 13.00 ± 4.1 | 18.33 ± 5.95 | 9.50 ± 4.62 |
| Grade 3 | 5.55 ± 5.55 | 0 ± 0.0 | 31.67 ± 14.19 | 8.50 ± 7.46 | 36.11 ± 14.88 | 10.50 ± 9.44 |
| SCORE | 62.67 ± 18.64 | 16.1 ± 5.2* | 33.00 ± 6.44 | 15.70 ± 5.22 | 37.78 ± 5.58 | 24.45 ± 4.62 |

*Indicates significant ($p < 0.05$) difference between the groups tested.

TABLE 3

Brown-Norway rat kidneys transplanted into Lewis rats. Summary of histological analysis of the effects of Met-RANTES on vascular and tubular damage, and interstitial mononuclear infiltration in the presence of low dose CyA.

| SCORE | Cyclosporin 2.5 mg/kg b.w./d | Cyclosporin 2.5 mg/kg b.w./d + Met-RANTES 50 μg/d |
| --- | --- | --- |
| VASCULAR INJURY | 60.7 ± 1.8 | 13.7 ± 7.5* |
| Tubular Damage | 124.3 ± 28.7 | 28.3 ± 14.8* |
| Interstitial Inflammation | 157.3 ± 21.3 | 71 ± 6.1* |

*Indicates significant ($p < 0.05$) difference between the groups tested.

TABLE 4

Effect of IL-1β on the surface expression of adhesion molecules in human microvascular endothelial cells. DMVEC were activated with IL-1β (5 ng/ml) or left untreated (control) for 12 hr., and were reacted with ICAM-1, VCAM-1, E-selectin or isotype control mAbs. The surface protein expression was analysed by FACS in 3 independent experiments and given as specific mean fluorescence intensity (sMFI) after correction for unspecific binding in channels.

| SMFI (channels) |  | Control | IL-1β |
| --- | --- | --- | --- |
| ICAM-1 | Exp. 1 | 339 | 502 |
|  | Exp. 2 | 386 | 592 |
|  | Exp. 3 | 327 | 432 |
| VCAM-1 | Exp. 1 | 10 | 76 |
|  | Exp. 2 | 72 | 236 |
|  | Exp. 3 | 25 | 129 |
| E-selectin | Exp. 1 | 1 | 120 |
|  | Exp. 2 | 44 | 265 |
|  | Exp. 3 | 28 | 177 |

REFERENCES

Bishop G. A. et al., *Kidney Int.*, 29, 708–717, 1986.
Butcher E. C., *Cell*, 67, 1033–1036, 1991.
Butcher E. C. et al., *Science*, 272, 60–66, 1996.
Castro M. D. et al., *Transpl. Int.*, 111, S15–S18, 1998.
Devergne O. et al., *J. Exp. Med.*, 179, 1689–1694, 1994.
Erl W. et al., *Atherosclerosis*, 113, 99–107, 1995.
Fisher B. et al., *Surgery*, 58, 904–917, 1965.
Gong J. H. et al., *J. Biol. Chem.*, 271, 10521–10527, 1996.
Gröne H. J., *Neph. Dial. Transplant*, 11, 1916–1917, 1996.
Kukerti S. et al., *Blood*, 89, 4104–4111, 1997.
Lloyd C. M et al., *J. Exp. Med.*, 185, 1371–1380, 1997.
Lloyd C. M. et al., *J Leukoc. Biol.*, 62, 676–680, 1997.
Luckas N. W. et al., *J Leukoc. Biol.*, 59, 13–17, 1996.
Luscinskas F. W. et al., *J. Immunol.*, 156, 326–335, 1994.
Luster A. D., *N. Engl. J. Med.*, 338, 436–445, 1998.
Martindale, The Extra Pharmacopoeia, 31th edition, London, Royal Pharmaceutical Industry, 1996, 557–562.
Nelson P. J. et al., *Curr. Opin., Immunol.*, 10, 265–270, 1998.
Nelson P. J. et al., The Chemokine RANTES. In Cytokines, Handbook of Immunopharmacology Series. R. Thorpe and A. Mire-Sluis, editors. Academic Press. London. 433–448, 1998.
Nibbs R. J. et al., *J. Biol. Chem.*, 272, 32078–32083, 1997.
Nickerson P. et al., *Transplantation*, 27, 489–494, 1997.
Pattison J. et al., *Lancet*, 343, 209–211, 1994.
Piali L. et al., *Eur. J. Immunol.*, 28, 961–972, 1998.
Plater-Zyberk C. et al., *Immunol. Lett.*, 57, 117–120, 1997.
Proudfoof A. E. et al., *J. Biol. Chem.*, 271, 2599–2603, 1996.
Schlöndorff D. et al., *Kidney Int.*, 51, 610–621, 1997.
Schmouder R. L. et al., *Nephrol. Dial. Transplant.*, 10 Suppl 1, 36–43, 1995.
Simmons G. et al *Science*, 276, 276–279, 1997.
Simon M. et al., *Am. J. Physio.*, 268, F240–F250, 1995.
Springer T. A., *Cell*, 76, 301–314, 1994.
Stojanovic T. et al., *Lab. Invest.*, 74, 496–512, 1996.
Strom T. B. et al., *Curr. Opin. Immunol.*, 8, 688–693, 1996.
Teixeira M. M et al., *J. Clin. Invest.*, 100, 1657–1666, 1997.
Valente J. F. et al., *Surg. Clin. North Am.*, 78, 1–26, 1998.
Von Luettichau I., et al., *Cytokine*, 8, 89–98, 1996.
Weber C. et al., *Eur. J. Immunol.*, 23, 852–859, 1993
Weber C. et al., *J. Immunol.*, 155, 445–451, 1995.
Weber C. et al., *J. Clin. Invest.*, 100, 2085–2093, 1997.
Wiedermann C. J. et al., *Curr. Biol.*, 3, 735–739, 1993.
Ziegler-Heitbrock H. W. L. et al., *Internat. J. Cancer*, 41, 456–461, 1988.

What is claimed is:

1. A method of treating or preventing the rejection of transplanted organs, tissues or cells which comprises administering to a subject in need thereof (1) a chemokine receptor antagonist for the RANTES receptors said antagonist selected from the group consisting of Met-RANTES, Leu-RANTES, Gln-RANTES, amino terminally truncated RANTES missing the first two amino acid residues, amino terminally truncated RANTES missing the first five amino acid residues, amino terminally truncated RANTES missing the first six amino acid residues, amino terminally truncated RANTES missing the first seven amino acid residues, amino terminally truncated RANTES missing the first eight amino acid residues, and amino terminally truncated RANTES missing the first nine amino acid residues and (2) a cyclosporin to treat or prevent the rejection of transplanted organs, tissues or cells.

2. The method according to claim 1, wherein the rejection treated or prevented is renal allograft transplantation rejection.

3. The method according to claim 1, wherein the chemokine receptor antagonist and cyclosporin are administered simultaneously.

4. The method according to claim 1, wherein the chemokine receptor antagonist and cyclosporin are administered sequentially or separately.

5. The method according to claim 1, wherein the chemokine receptor antagonist is Gln-RANTES.

6. The method according to claim 1, wherein the chemokine receptor antagonist is Leu-RANTES.

7. The method according to claim 1, wherein the chemokine receptor antagonist is Met-RANTES.

8. The method according to claim 1, wherein the cyclosporin is cyclosporin A.

9. The method according to claim 8, wherein the chemokine receptor antagonist is Met-RANTES.

10. The method according to claim 9, wherein the rejection treated or prevented is renal allograft transplantation rejection.

11. A pharmaceutical composition comprising at least one pharmaceutically acceptable excipient and the combination of (1) a chemokine receptor antagonist for the RANTES receptors said antagonist selected from the group consisting of Met-RANTES, Leu-RANTES, Gln-RANTES, amino terminally truncated RANTES missing the first two amino acid residues, amino terminally truncated RANTES missing the first five amino acid residues, amino terminally truncated RANTES missing the first six amino acid residues, amino terminally truncated RANTES missing the first seven amino acid residues, amino terminally truncated RANTES missing the first eight amino acid residues, and amino acid residues terminally truncated RANTES missing the first nine and (2) a cyclosporin.

12. The pharmaceutical composition according to claim 11, wherein the chemokine receptor antagonist is Gln-RANTES.

13. The pharmaceutical composition according to claim 11, wherein the chemokine receptor antagonist is Leu-RANTES.

14. The pharmaceutical according to claim 11, wherein the chemokine receptor antagonist is Met-RANTES.

15. The pharmaceutical composition according to claim 11, wherein the cyclosporin is cyclosporin A.

16. The pharmaceutical composition according to claim 15, wherein the chemokine receptor antagonist is Met-RANTES.

* * * * *